United States Patent
Ostafin et al.

(10) Patent No.: US 9,956,180 B2
(45) Date of Patent: May 1, 2018

(54) METHOD AND APPARATUS FOR CONTINUOUS REMOVAL OF SUB-MICRON SIZED PARTICLES IN A CLOSED LOOP LIQUID FLOW SYSTEM

(71) Applicant: Nanoshell Company, LLC, North Salt Lake, UT (US)

(72) Inventors: Agnes Ostafin, North Salt Lake, UT (US); Hiroshi Mizukami, Pasadena, CA (US)

(73) Assignee: NANOSHELL COMPANY, LLC, North Salt Lake, UT (US)

( * ) Notice: Subject to any disclaimer, the term of this patent is extended or adjusted under 35 U.S.C. 154(b) by 218 days.

(21) Appl. No.: 14/803,361

(22) Filed: Jul. 20, 2015

(65) Prior Publication Data
US 2015/0321204 A1 Nov. 12, 2015

Related U.S. Application Data

(63) Continuation-in-part of application No. 13/322,790, filed as application No. PCT/US2010/046421 on Aug. 24, 2010, now abandoned.
(Continued)

(51) Int. Cl.
*B04B 7/08* (2006.01)
*A61K 9/51* (2006.01)
(Continued)

(52) U.S. Cl.
CPC .......... *A61K 9/5192* (2013.01); *A61K 9/0026* (2013.01); *A61K 9/5115* (2013.01);
(Continued)

(58) Field of Classification Search
CPC .............. A61M 1/3679; A61M 1/3687; A61M 1/3693; A61M 1/3696; B01D 21/262;
(Continued)

(56) References Cited

U.S. PATENT DOCUMENTS 4,387,848 A 6/1983 Kellogg et al.
4,479,790 A 10/1984 Bocckino et al.
(Continued)

FOREIGN PATENT DOCUMENTS

CA 1298822 4/1992
CN 101172207 5/2008
(Continued)

OTHER PUBLICATIONS

Andres, et al., "Anisotropic Calcium Phosphate Nanoparticles Coated with 2-Carboxyethylphosphonic Acid", J. Mater. Chem. vol. 16, 2006, 3964-3968.
(Continued)

*Primary Examiner* — Timothy C Cleveland
(74) *Attorney, Agent, or Firm* — Peacock Law P.C.; Janeen Vilven (57) ABSTRACT

A method and apparatus for continuous removal of sub-micron sized particles and other materials attached thereto such as cancer cells and bacteria from blood and other liquids. A centrifuge rotor having a curved shape is offset on a spinning rotor base and creates contiguous areas of low to high centrifugal force depending on the distances from the axis of the rotor base. This creates a density gradient field that separates materials of different densities input to the centrifuge that exit via different outputs. A monitor detects components of the fluid that are mixed with the particles before they exit the centrifuge. If there are any unwanted components detected with the particles logic circuitry changes the speed of rotation of the rotor, and the flow rate of pumps inputting and removing separated fluid and particles to and from the centrifuge until there are no unwanted components in the fluid exiting with the particles from the centrifuge.

22 Claims, 2 Drawing Sheets

Related U.S. Application Data (60) Provisional application No. 61/236,810, filed on Aug. 25, 2009.

(51) Int. Cl.
  *A61K 9/00* (2006.01)
  *A61K 38/42* (2006.01)
  *B04B 5/04* (2006.01)
  *B04B 13/00* (2006.01)
  *A61K 31/01* (2006.01)
  *A61M 1/36* (2006.01)
  *B01D 21/26* (2006.01)
  *B01D 21/34* (2006.01)
  *A61K 9/50* (2006.01)

(52) U.S. Cl.
  CPC .......... *A61K 9/5123* (2013.01); *A61K 9/5146* (2013.01); *A61K 9/5169* (2013.01); *A61K 31/01* (2013.01); *A61K 38/42* (2013.01); *A61M 1/3679* (2013.01); *A61M 1/3687* (2013.01); *A61M 1/3693* (2013.01); *A61M 1/3696* (2014.02); *B01D 21/262* (2013.01); *B01D 21/34* (2013.01); *B04B 5/0442* (2013.01); *B04B 7/08* (2013.01); *B04B 13/00* (2013.01); *A61K 9/5073* (2013.01); *B04B 2005/045* (2013.01); *B04B 2013/006* (2013.01)

(58) Field of Classification Search
  CPC ......... B01D 21/34; B04B 5/0442; B04B 7/08; B04B 13/00; B04B 2005/045; B04B 2013/006

See application file for complete search history.

(56) References Cited

U.S. PATENT DOCUMENTS

| | | | |
|---|---|---|---|
| 5,123,901 | A | 6/1992 | Carew |
| 5,386,734 | A | 2/1995 | Pusinelli |
| 5,635,207 | A | 6/1997 | Grinstaff et al. |
| 5,641,622 | A | 6/1997 | Lake et al. |
| 5,663,051 | A | 9/1997 | Vlasselaer |
| 5,679,394 | A | 10/1997 | Long, Jr. et al. |
| 5,811,521 | A | 9/1998 | Kluger et al. |
| 5,840,502 | A | 11/1998 | Van Vlasselaer |
| 6,071,422 | A | 6/2000 | Hlavinka et al. |
| 6,277,060 | B1 | 8/2001 | Neumann |
| 6,280,375 | B1 | 8/2001 | Meisberger et al. |
| 6,416,456 | B2 | 7/2002 | Zanella et al. |
| 6,497,674 | B1 | 12/2002 | Steele et al. |
| 7,297,272 | B2 | 11/2007 | Min et al. |
| 7,531,133 | B2 | 5/2009 | Hole |
| 2003/0026024 | A1 | 2/2003 | Igarashi |
| 2003/0026855 | A1 | 2/2003 | Kameneva et al. |
| 2003/0036518 | A1 | 2/2003 | Samain et al. |
| 2004/0102732 | A1 | 5/2004 | Naghavi et al. |
| 2005/0087122 | A1 | 4/2005 | Ismagilov et al. |
| 2006/0003439 | A1 | 1/2006 | Ismagilov et al. |
| 2006/0240964 | A1 | 10/2006 | Lolachi et al. |
| 2006/0280798 | A1 | 12/2006 | Ensoli |
| 2007/0026024 | A1 | 2/2007 | Drees |
| 2007/0258888 | A1 | 11/2007 | Feldmann |
| 2009/0088679 | A1 | 4/2009 | Wood et al. |
| 2011/0201986 | A1 | 8/2011 | Howell et al. |
| 2011/0224645 | A1 | 9/2011 | Winqvist et al. |
| 2012/0077662 | A1 | 3/2012 | Ostafin et al. |
| 2012/0164231 | A1 | 6/2012 | Ostafin et al. |
| 2014/0008301 | A1 | 1/2014 | Ostafin et al. |
| 2015/0238432 | A1 | 8/2015 | Ostafin et al. |
| 2016/0038668 | A1 | 2/2016 | Ostafin et al. |

FOREIGN PATENT DOCUMENTS

| | | |
|---|---|---|
| CN | 101322029 | 12/2008 |
| EP | 0416575 | 3/1991 |
| WO | 1995/528915 | 11/1995 |
| WO | 1999/002269 | 1/1999 |
| WO | 2005/097208 | 10/2005 |
| WO | 2006/020100 | 2/2006 |
| WO | 2006/115938 | 11/2006 |
| WO | 2008/107167 | 9/2008 |
| WO | 2011/025755 | 3/2011 |
| WO | 2011/025756 | 3/2011 |
| WO | 2014/008490 | 1/2014 |

OTHER PUBLICATIONS

Baran, et al., "Detection of Cancer Cells in the Blood by FACS Sorting of CD45-Cells", Int. J. Mol. Med., vol. 1, No. 3, 1998, 573-581.

Beltinger, et al., "A Simple Combined Microdissection and Aspiration Device for the Rapid Procurement of Single Cells from Clinical Peripheral Blood Smears", Mol. Path., vol. 51, No. 4, 1998, 233-236.

Brandt, et al., "Two-Layer Buoyant Density Centrifugation Gradient for Enrichment of Prostate-Derived Cells and Cell Clusters from Peripheral Blood", Clinical Chemistry, vol. 42, No. 11, 1996, 1881-1882.

Brugger, et al., "Mobilization of Tumor Cells and Hematopoietic Progenitor Cells Into Peripheral Block of Patients With Solid Tumors", Blood, vol. 83, No. 3, 1994, 636-640.

Buckner, et al., "Leukapheresis by Continuous Flow Centrifugation (CFC) in Patients with Chronic Myelocytic Leukemia (CML)", Blood, vol. 33, 1969, 353-369.

Campana, et al., "Detection of Minimal Residual Disease in Acute Leukemia: Methodologic Advances and Clinical Significance", Blood, vol. 85, No. 6, 1995, 1416-1434.

Chang, "Blood Substitutes Based on Nanobiotechnology", Trends in Biotechnology, vol. 24, No. 8, 2006, 372-377.

Denis, et al., "Detection of Disseminated Tumor Cells in Peripheral Blood of Colorectal Cancer Patients", Int J Cancer, vol. 74, No. 5, 1998, 540-544.

Glaves, et al., "Haematogenous Dissemination of Cells from Human Renal Adenocarcinomas", Br J Cancer, vol. 57, 1988, 32-35.

Harlozinska, et al., "Density Distribution, Cytomorphologic Features and Immunologic Characteristics of Ovarian and Endometrial Clear Cell Carcinomas", Acta Cytologica, vol. 34, No. 5, 1990, 657-663.

Henkel-Hanke, et al., "Artificial Oxygen Carriers: A Current Review", AANA Journal, vol. 75, No. 3, 2007, 205-211.

Hester, et al., "Principles of Blood Separation and Component Extraction in a Disposable Continuous-Flow Single-Stage Channel", Blood, vol. 54, No. 1, 1979, 254-268.

Hill, "Oxygen Therapeutics—Current Concepts", Canadian Journal of Anaesthesia, vol. 48, No. 4, 2001, S32-S40.

Jahr, "Blood Substitutes as Pharmacotherapies in Clinical Practice", Curr Opin Anaesthesiology, vol. 20, No. 4, 2007, 325-330.

Judson, et al., "Closed Continuous-Flow Centrifuge", Nature vol. 217, 1968, 816-818.

Kabalnov, et al., "Phospholipids as Emulsion Stabilizers. 1. Interfacial Tensions", Langmuir, vol. 11, No. 8, 1995, 2966-2974.

Karczewski, et al., "The Efficiency of an Autotransfusion System for Tumor Cell Removal from Blood Salvaded During Cancer Surgery", Anesth Analg, vol. 78, No. 6, 1994, 1131-1135.

Keipert, "OxygentTM, a Perfluorochemical-Based Oxygen Therapeutic for Surgical Patients", Blood Substitutes, Chapter 28, 2006, 312-323.

Kim, et al., "Artificial Oxygen Carriers as Red Blood Cell Substitutes: a Selected Review and Current Status", Artificial Organs, vol. 28, No. 9, 2004, 813-828.

Klein, et al., "Transperitoneal Oxygenation with Fluorocarbons", Anesthesia and Analgesia, vol. 65, No. 7, 1986, 734-738.

Koch, et al., "Duration of Red-Cell Storage and Complications after Cardiac Surgery", N Engl J Med, vol. 358, 2008, 1229-1239.

(56) References Cited

OTHER PUBLICATIONS

Ness, "Oxygen Therapeutics-Pursuit of an Alternative to the Donor Red Blood Cell", Arch Pathol Lab Med, vol. 131, No. 5, 2007, 734-741.

Ng, et al., "Buoyant Density of EMT6 Fibrosarcoma Cells", Cell Biophysics, vol. 2, No. 2, 1980, 153-163.

Racila, et al., "Detection and Characterization of Carcinoma Cells in the Blood", Proc Natl Acad Sci, vol. 95, No. 8, 1998, 4589-4594.

Sabile, "Efficiency of Ber-EP4 Antibody for Isolating Circulating Epithelial Tumor Cells Before TR-PCR Detection", Am J Clin Pathol, vol. 112, No. 2, 1999, 171-178.

Schmidt, "Calcium Phosphate Based Nanoshell for use in Biomedical Applications", University of Notre Dame Electronic Theses & Disertations, 2006, 1-347.

Suarez-Quian, "Laser Capture Microdissection of Single Cells from Complex Tissues", Biotechniques, vol. 26, No. 2, 1999, 328-335.

Thomas, et al., "Purification of Hematopoietic Stem Cells for Further Biological Study", Methods, vol. 17, No. 3, 1999, 202-218.

METHOD AND APPARATUS FOR CONTINUOUS REMOVAL OF SUB-MICRON SIZED PARTICLES IN A CLOSED LOOP LIQUID FLOW SYSTEM

CROSS REFERENCE TO RELATED APPLICATIONS

This application is a Continuation-in-Part of U.S. patent application Ser. No. 13/322,790, entitled "Method and Apparatus for Continuous Removal of Submicron Sized Particles in a Closed Loop Liquid Flow System", filed on Nov. 28, 2011, which is a National Stage Entry of International Patent Application PCT/US10/46421, entitled "Method and Apparatus for Continuous Removal of Sub-micron Sized Particles in a Closed Loop Liquid Flow System, filed on Aug. 24, 2010, which claims priority to and the benefit of U.S. Provisional Patent Application Ser. No. 61/236,810, entitled "Synthesis of Oxygen Carrying, Turbulence Resistant High Density Submicron Particulates and Method for Their Continuous Retrieval from the Blood Including Submicron Size Perfluorocarbon Emulsion and PolyHb Dual-Cored Oxygen Carries (DCOC)", filed on Aug. 25, 2009. The specification and claims thereof are incorporated herein by reference.

FIELD OF THE INVENTION

The present invention relates to a method and apparatus for continuous removal of sub-micron sized particles from the blood or other liquids.

BACKGROUND OF THE INVENTION

The blood consists of wide ranges of cells, molecules, ions and water. But, their abnormal degradation or proliferation, their functional changes, and invasion of foreign matters or toxins into the blood call for immediate intervention. Removing unwanted materials from the blood is a solution. Embodiments of the present invention provides for a system and method to specifically remove unwanted targets in the blood by attaching the unwanted target to a high density sub-micron particle and separating the high density sub-micron particle from the blood with density dependent centrifugation. An embodiment of a device as disclosed herein will also be capable of removing specific targets from other liquids and solvents after the targets have been attached to a high density sub-micron particle functionalized to bind to the specific target.

A high density sub-micron particle as referenced herein may have intrinsic biological function, such as use as a perfluorocabon based artificial oxygen carrier (AOC). After some time, the AOC may have to be centrifugally collected from the blood and removed, by taking advantage of their density being higher than that of the blood components.

The benefits of other types of high density sub-micron particles may be found in their ability to capture the desired targets after the sub-micron high density particles are functionalized to conjugate with the specific cells, molecules and ions in the blood. The sub-micron high density particles may be able to capture the circulating tumor cells (CTC), sickle cell hemoglobin (HbS), toxins, irons etc. in the blood and then be retrieved from the circulation using the specialized centrifuge rotor described herein, after the targets bind to the binding partner located on a sub-micron high density particles.

Removing the sub-micron high density particles as described herein will be possible with aphaeresis instruments of various types already available. However, the instruments already available are tuned for separating molecules and cells found in blood which span a limited range of densities. The densities of sub-micron particles of interest are 1.9 gm/ml or higher and are significantly higher than those of the highest density component found in blood, namely 1.2 g/ml of RBC, and most synthetic organic and polymeric materials. Separating materials with such large differences in density is carried out with a rotor as described herein rather than those described for use in conventional clinical aphaeresis instruments.

An embodiment of a rotor as described herein will continuously or intermittently isolate high density sub-micron particles from blood components (for example whole blood or subfraction thereof) continuously and quickly. In one embodiment, since the separation is continuous, there will be no limits in the volume of materials to be centrifuged. In one embodiment of the rotor, the volume of rotor is no more than about 15 mls and counting the volumes of the tubes that provide flow to the rotor and the tubes that direct the liquid from the rotor through the treatment process the volume will be less than 70 mls. Thus, the volume of exo-corporeal treatment will be about 85-100 mls. In another embodiment the rotor can be used to continuously or intermittently isolate high density sub-micron particles from other biological fluids, cell lysates, macromolecule or polymer solutions etc.

SUMMARY OF THE INVENTION

One embodiment of the present invention provides for a rotor for a centrifuge used to separate a mixture of components in a fluid having different densities, the rotor comprising a rotor base having a central axis and the rotor base is rotated about the central axis when the centrifuge is in use. A first rotor element that is curved and is attached to and has an orientation extending away from the rotor base, the first rotor element having a first end and a second end; and a second rotor element that is curved and is attached to and has an orientation extending away from the rotor base, the second rotor element having a first end and a second end, the second end of the first rotor element being connected to the first end of the second rotor element to form a composite rotor element; wherein the composite rotor element is positioned on the rotor base so that the first end of the first rotor element and the second end of the second end of the second rotor element are at different distances from the central axis wherein the composite rotor element traverses 180° or less around the axis of rotation of the rotor base. The rotor base with composite rotor element mounted thereon is rotated the orientation of the composite rotor element on the rotor base and creates a density gradient that separates two components of the mixture of components that is input to the composite rotor element, where the two components have different densities, and a first of the two components moves in a first direction inside composite rotor element and is removed from the composite rotor element at the first output port while a second of the two components moves in a second, opposite direction inside the composite rotor element and is removed from the composite rotor element at the second output port.

Optionally a monitor port through the sidewall of composite rotor element can be included, the monitor port being closer to the second output port at the second end of the second rotor element than the input port is, the monitor port being used to extract a sample of the second of the two components moving toward the second output port, the sample being used to determine if the first of the two components has been separated from the second component. In addition an outwardly extending end at the first end of the first rotor segment and at the second end of the second rotor segment can be included, wherein as the rotor these two ends create a pressure pushing the first component of the mixture of components toward the first output port and pushing the second component of the mixture of components toward the second output port. A sensor can be connected to the monitor output port to monitor the sample of the second of the two components moving toward the second output port and extracted at the monitor port for the presence of any of the first of the two components, the sensor generating an output signal if any of the first of the two components is present; and electronics receiving the output signal from the sensor, the electronics causing a change in the rate at which the first of the two components is removed from the centrifuge at the first output port, and changing the rate at which the second of the two components is removed from the centrifuge at the second output port to eliminate the presence of any of the first of the two components in the sample taken at the monitor output port, thus assuring there is none of the first of the two components present with the second of the two components exiting the centrifuge at the second output port. The electronics can also cause a change in the rate at which the mixture of components is input to the composite rotor element to assure there is none of the first of the two components present with the second of the two components exiting the composite rotor element at the second output port.

Additionally, a monitor port through the sidewall of the composite rotor element, the monitor port being closer to the second output port at the second end of the second rotor element than the input port is, the monitor port being used to extract a sample of the second of the two components moving toward the second output port, the sample being used to determine if the first of the two components has been separated from the second component. Further still, an outwardly extending end at the first end of the first rotor segment and at the second end of the second rotor segment is included, wherein as the rotor turns these two ends create a pressure pushing the first component of the mixture of components toward the first output port and the second component of the mixture of components toward the second output port. The rotor base with composite rotor element mounted thereon is rotated the orientation of the composite rotor element on the rotor base creates a density gradient that separates two components of the mixture of components that is input to the centrifuge housing, where the two components have different densities, and a first of the two components moves in a first direction inside the centrifuge housing and is removed from the centrifuge housing at the first output port while a second of the two components moves in a second, opposite direction inside the centrifuge housing and is removed from the centrifuge housing at the second output port. In addition, a sensor connected to the monitor output port to monitor the sample of the second of the two components moving toward the second output port and extracted at the monitor port for the presence of any of the first of the two components, the sensor generating an output signal if any of the first of the two components is present; and electronics receiving the output signal from the sensor, the electronics causing a change in the rate at which the first of the two components is removed from the centrifuge at the first output port, and changing the rate at which the second of the two components is removed from the centrifuge at the second output port to eliminate the presence of any of the first of the two components in the sample taken at the monitor output port, thus assuring there is none of the first of the two components present with the second of the two components exiting the component rotor element at the second output port. The electronics can also causes a change in the rate at which the mixture of components is input to the component rotor element to assure there is none of the first of the two components present with the second of the two components exiting the component rotor element at the second output port.

Another embodiment provides a rotor for a centrifuge used to separate whole blood from other artificial blood having a density higher than any of the components of the whole blood, the rotor comprising a rotor base having a central axis and the rotor base is rotated about the central axis when the centrifuge is in use; a first rotor element that is curved and is attached to and has an orientation extending away from the rotor base, the first rotor element having a first end and a second end; and a second rotor element that is curved and is attached to and has an orientation extending away from the rotor base, the second rotor element having a first end and a second end, the second end of the first rotor element being connected to the first end of the second rotor element to form a composite rotor element; wherein the composite rotor element is positioned on the rotor base so that the first end of the first rotor element and the second end of the second end of the second rotor element are at different distances from the central axis wherein the composite rotor traverses about 180° around the axis of rotation of the rotor base and contains a chamber therein.

The rotor base with composite rotor element mounted thereon is rotated, and the orientation of the composite rotor element on the rotor base creates a density gradient that separates the whole blood from the artificial blood where the components of the whole blood have a lower density than the artificial blood, and a first of the whole blood moves inside the composite rotor element toward and is removed from the composite rotor element at the first output port while the artificial blood moves inside the composite rotor element and is removed from the composite rotor element at the second output port. Additionally, a monitor port through the sidewall of the component rotor element is added, the monitor port being closer to the second output port at the second end of the second rotor element than the input port is, the monitor port being used to extract a sample of the artificial blood moving toward the second output port, the sample being used to determine if the whole blood has been completely separated from the artificial blood. Further, an outwardly extending end at the first end of the first rotor segment and at the second end of the second rotor segment can be included, wherein as the rotor turns, these two ends create a pressure pushing the whole blood toward the first output port and the artificial blood toward the second output port. Further still, a sensor connected to the monitor output port to monitor the sample of the artificial blood moving toward the second output port and extracted at the monitor port to test for the presence of any whole blood components, the sensor generating an output signal if any of the whole is present; and electronics receiving the output signal from the sensor, the electronics causing a change in the rate at which the whole blood is removed from the centrifuge at the first output port, and changing the rate at which the artificial blood is removed from the centrifuge at the second output port to eliminate the presence of any of the whole blood in the sample taken at the monitor output port, thus assuring there is none of the first of the two components present with the second of the two components exiting the centrifuge at the second output port. The electronics can also causes a change in the rate at which the mixture of whole blood and artificial blood is input to the composite rotor element to assure there is none of the whole blood components present with the artificial blood exiting the composite rotor element at the second output port.

In another embodiment a method of separating components in a fluid based upon a difference in density of the components in the fluid when the components are mixed together comprising the steps of providing to a rotor as described herein the fluid containing the mixed together components to be separated based upon the difference in density of the mixed together components and continuously flowing the components in the fluid to the rotor while the rotor is spinning. The components in the fluid are separated based upon the difference in density of the mixed together components with the use of centrifugal force when the rotor is spinning. The components having a first density are collected via a first tube located at a first position on the rotor and the components having a second density are collected via a second tube located at a second position on the rotor and a the components having a third density are collected via a third tube at a third position on the rotor. The components having a first density comprise high density sub-micron particles that have a density different than the components with a second density or a third density and wherein the high density sub-micron particles are functionalized to capture a first component from the components mixed together in the fluid.

DESCRIPTION OF THE DRAWINGS

The invention will be better understood upon reading the following Detailed Description in conjunction with the drawings in which.

DETAILED DESCRIPTION

As used herein "a" and "the" means one or more unless otherwise specified.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary. Furthermore, the use of the term "including", as well as other related forms, such as "includes" and "included", is not limiting.

During the continuous flow of liquid, a rotor as described herein is spinning and designed to separate the components of the liquid according to the densities of components located within the fluid and collect the components of highest, lowest and other defined densities via tubes. The blood or other fluid or solution having components to be separated will enter through a port (for example near in the middle of the rotor) and the components will be separated to high density on one end of the rotor and low density on the other end. Components with densities between the two limits will concentrate at a position between the two ends for example near in the middle of the rotor. The three different density fractions will leave through their own ports. The entering flow rate of blood or other fluid solution will often be determined by an external requirement such as the status of a patient and the desired purity of separation. The flow rate can be adjusted by a dedicated pump. In one embodiment to adjust the exit flow rates through all three exit ports only two pumps are used. The rate of each outward flow rate will be defined by the type of high-density sub-micron particles used (i.e whether or not it is surface activated to capture a target substance), the amounts of target expected to be captured by the sub-micron particles, and the source fluid. Typically, the rate of flow of a fluid such as blood entering the rotor should be in compatible with the rates of blood flows in the blood vessels of the subject, around 32 ml/min. Thus total flow rate from the three output ports should be 32 ml/min according to one embodiment of the present invention. In one embodiment, the flow rate through each tube carrying fluid to and away from the rotor will be limited by mechanism employed to ensure that the entering and exit tubes remain kink-free as the rotor spins (several methods are currently used in aphaeresis systems). The rotor and method as described according to one embodiment of the present invention distinguishes itself from other clinical aphaeresis rotors by collecting all of the naturally occurring components of blood in a single flow path, separate from materials with buoyant densities higher than 1.2 g/ml. In the event these particles are designed to attach to a specific naturally occurring blood component, then that component will also be separated along with the particles from naturally occurring components of blood. Such particles are referred to as centrifugally retrievable target activated sub-micron particles, thus rTAP and have a density higher than the density of naturally occurring components of blood. Examples of cells, molecules, and ions that can be continuously retrieved with the proposed centrifugal device from the circulating blood include circulating tumor cells, ABO type red blood cells, macrophages, sickle cell hemoglobin, AOC, antigens, antibodies, drugs, toxins, and irons but are not limited thereto.

A rotor according to one embodiment of the present invention would be able to separate continuously any particles in the flowing liquid through the rotor according to their densities when the system is exerting centrifugal force on the liquid. As the densities of targeted cells and molecules are sufficiently made higher by attaching to the retrievable high density sub-micron particles such as nanoparticles (referred to herein as high-density, retrievable sub-micron particles or rP), the target cells and molecules would establish their unique density profile of relative narrow range that can be separated with the proposed device. Retrieval of particle bound CTC, HbsS, AOC, by itself acting as high density sub-micron particles (see U.S. patent application publication US 2012/0164231 and US 2014/0008301) would offer significant benefit to the patient. The components bound to such particles will be referred to as targets and target activated rP will be referred to as rTAP, here after.

Figure 1:
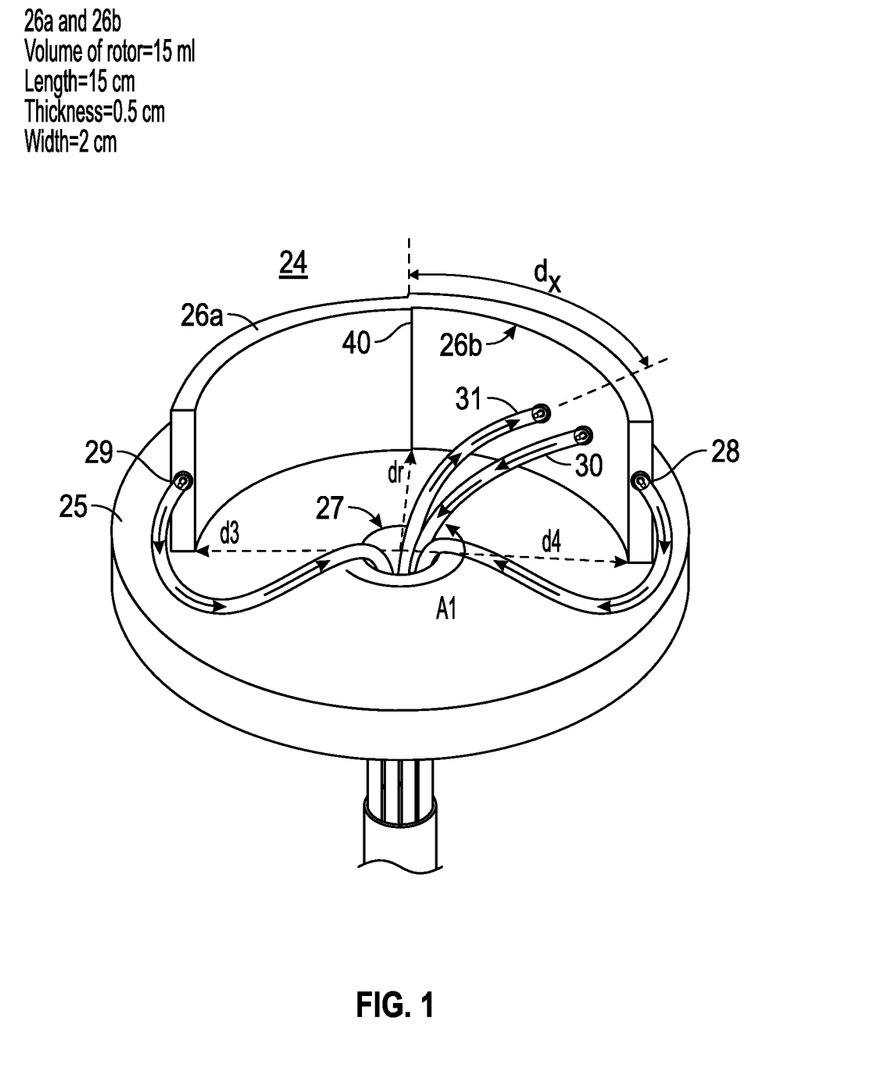
FIG. 1 is a perspective view of the novel centrifuge that utilizes density gradient separation to efficiently remove particulate artificial oxygen carriers from blood or other biofluids.

Referring now to FIG. 1, an embodiment of the rotor is illustrated. The case of the centrifuge is not shown in FIG. 1 to make the drawing simpler so the invention can be better understood. Rotor 24 comprises a circular rotor base 25 that is mounted on an axis 27 to a motor driven shaft (not shown). As shown in FIG. 1 rotor base 25 is rotated in a counter clockwise direction for the rotor 24 configuration shown and described herein. The blood mixed with high density particles (rP or rTAP) enter at port 31 of the rotor consisting of elements 26a and 26b and their position on rotor base 25, to create a density based gradient that separates RBC, of which light density plasma exits at port 29 and the high density particles (with or without targets depending on the desired outcome) exits from port 28, while from a mixture of RBC and rTAP that is input to the centrifuge rotor at port 31. Distances d3, d4 and dr are shown in all of FIGS. 1, 2 and 3 to better understand how the rotor is placed on the base. In one embodiment of the present invention the rotor has a width of each rotor element 26a and 26b of 0.5 cm, the height is 2 cm, and the length is 15 cm. In one embodiment of the present invention, the volume of the rotor will be only 15 ml. As mentioned the procedure is continuous, but actual separation of components take place within this 15 ml of fluid within the rotor when spinning. The dimensions can be changed responding to the demand, but the same principles of centrifugation apply.

Rotor 24 is made up of two curved elements 26a and 26b that are joined together to form a total curved element of 180 degrees or less. The curvature of element 26b is slightly larger diameter than that of 26a generating slightly higher centrifugal force. The rotor is similar to that of a conventional aphaeresis instrument, but unlike the rotor of a conventional aphaeresis instrument the rotor of FIG. 1 is 180 degrees of circular rotor on the base and the blood flow rate from the rotor to a receptacle such as a patient is as fast as 32 ml/min. In one embodiment, the rotor can operate at 2400 rpm of spin speed to allow the density gradient to be quickly established and maintained, since the distance between the highest (1.2) and the lowest (1.0) density will be quickly established. Even in the presence of a density as high as 1.9 g/ml, the rotor density gradient will be quickly established and maintained. The density gradient difference between the highest and lowest is still about 0.9 g/ml, but it is spread over the entire length of the rotor (15 cm) to permit subtle difference in density to be recognized with this rotor 24. In one example, the complete blood enters from port 31 and because the rotor is off-centered from the axis of rotation, the high density components move towards the higher density, i.e. port 28, while the low density components (e.g. blood components) move towards port 29. Thus adjusting the relative flow rates of ports 28 and 29, it would be possible to adjust the profile of density gradient over the entire range of the rotor. In practice, the whole blood enters port 31 under the controlled flow rate by a pump. The flow rates of ports 28 and 29 can also be adjusted with a pair of pumps and the net rates of both pumps define the out flow of blood from the port 30, but the density of the particles at port 30 will be defined by the ratio of these two pumps. Thus, adjusting the rpm of the centrifuge, pumping rates at 31, 28 and 29, it would be possible to what should be the density of particles, which come out from the port 30 at the known flow rate. In practice, however, the instrument will be usually adjusted so that only the high density retrievable particles and any attached materials should appear from port 28.

Figure 2:
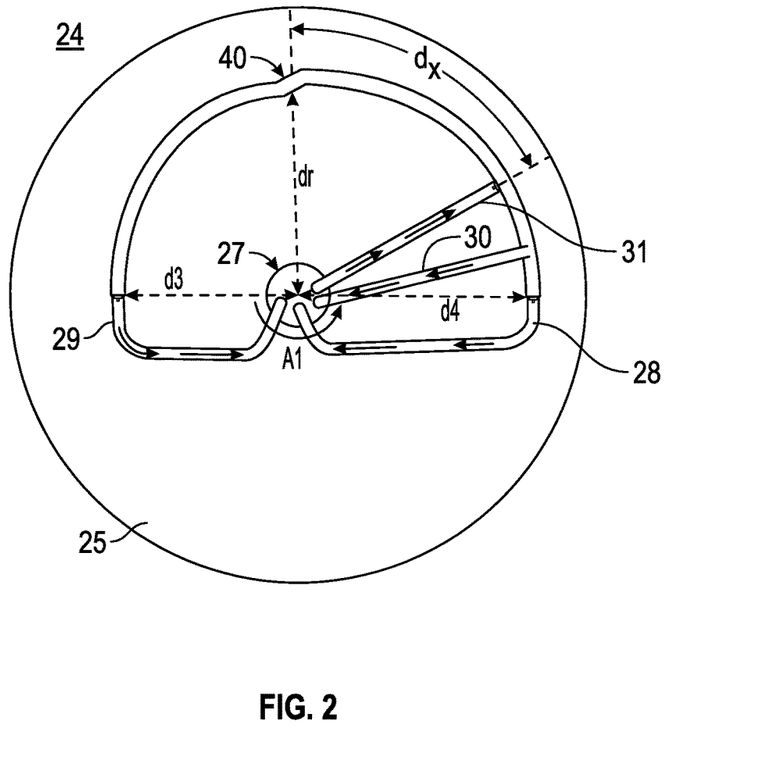
FIG. 2 is a top view of the novel centrifuge that better shows the novel rotor used in the centrifuge.

FIG. 2 is a top view of the novel centrifuge rotor 24 used in a centrifuge. As previously mentioned the different curvatures of rotor elements 26a and 26b and the offset of composite rotor element 26a,26b on rotor base 25 are best seen in FIG. 2. More particularly, rotor 26a,26b being belt shaped in the general shape of an ellipsoid with overlapping ends. With rotor 26a,26b being off centered on base 25 regions of high, medium and low centrifugal force are created depending on the distances from the axis of rotation 27. Input 31 where the composite mixture of RBC and rTAP is input to the centrifuge rotor is offset from the junction of rotor elements 26a and 26b and is closer to rTAP output port 28 by a circumferential distance "dx" as shown. In one embodiment the distance d3 is different from the distance d4. In one embodiment, the distance d3 is less than d4.

Figure 3:
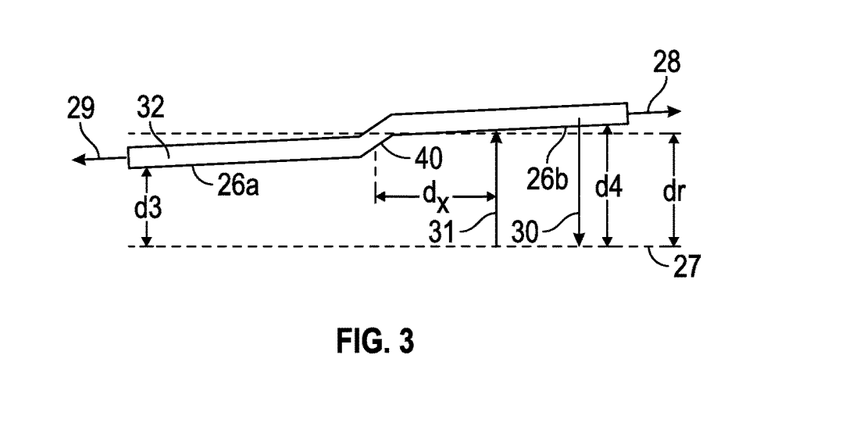
FIG. 3 is a linear graphical representation of the novel rotor of the centrifuge.

FIG. 3 is a linear graphical representation of the novel centrifuge rotor 24 of the centrifuge. This Figure shows how the distance between the face of composite rotor elements 26a,26b and the stretched form of the axis of rotation 27 of centrifuge rotor 24 changes. Thus, the magnitude of centrifugal force at different regions of centrifuge rotor 24 are depicted by the distance from the axis of rotation 27, which is stretched and shown as the dotted line at the bottom of FIG. 2. The distances d3, d4 and dr are shown in all of FIGS. 1, 2 and 3 to better understand how the figures relate to each other. The degree of change in distance is basically linear and in some embodiments close to flat except where rotor element 26a meets rotor element 26b. This is due to the fact the curvature of element 26a is different than the curvature of element 26b. In alternative embodiments of the invention the rate of change in distance may be uniform, and in another alternative embodiment the rate of change may be non-linear. Distances d3, d4 and dr between the face of rotor element 26a,26b and axis 27 are shown to link FIG. 3 with FIGS. 1 and 2. The input port 31 and output ports 28, 29 and 30 and their relative position with respect to the linear depiction of rotor 24 is shown according to one embodiment.

The whole blood including rTAP obtained from a person who is connected in a closed loop system with a density gradient centrifuge is input to the centrifuge rotor at input port 31. The whole blood is separated from the rTAP because the density of the rTAPs is greater than the density of the whole blood and any of its individual components. The whole blood is output at output port 29 and port 30 and is returned to the person from whom the blood and rTAP were withdrawn or stored in a container for later use. The rTAP is released from output port 28 and disposed. In addition, at a particular location near where the rTAP exits the centrifuge via rTAP output port 28, a small sample is removed from the density gradient centrifuge and exits the centrifuge at monitor output port 30. The sample is input to a red blood cell sensor of a control circuit to be checked for the presence of any remaining red blood cells (RBC) with the rTAP about to exit the centrifuge rotor. If any RBC are detected control circuit adjusts the speed of the blood and retrievable particle pumps that are part of circuit shown in FIG. 4 to permit the centrifuge rotor to fully separate any remaining RBC from the rTAP before the rTAP reaches monitor output port 30. This feedback operation assures that only rTAP exit output port 28.

The centrifugal field generated in the density gradient centrifuge as novel centrifuge rotor 24 turns about its axis 27 (FIGS. 1 and 2) creates a density gradient field that changes between output ports 28 and 29. Depending on the shape of rotor elements 26a and 26b, how they are joined, and how they are positioned on rotor base 25 this density field may change uniformly or it may non-linearly. The result is that the lower density whole blood fraction is separated from the higher density rTAP fraction. In an alternative embodiment another output port may be added somewhere between output ports 28 and 29 to separate intermediate density fractions of blood. The separated whole blood and rTAP are withdrawn through their respective output ports as previously described. The whole blood collected may be subjected to further fractionation. For example, further fractionation may be used to separate platelets and white blood cells from the whole blood in a manner known in the art.

The basic design of the centrifuge rotor 26a,26b is a belt shaped semicircular rotor placed slightly off-centered from the axis of rotation as shown in FIGS. 1 and 2. FIG. 1 is a three dimensional view of the rotor 26a,26b on the spinning rotor base 25, and FIG. 2 is a top view of rotor 26a,26b on the spinning rotor base 25. In FIG. 3 the rotor 26a,26b is shown stretched out in a linear configuration to help show the location of the rotor on rotor base 25 with respect to axis of rotation 27.

With reference to FIG. 3, as the centrifugation begins the rTAP of the input mixture 31 remain at the wall of the furthest out rotor segment 26b, as it is the most dense material and moves towards the higher centrifugal field. This is to the right in FIG. 3 and the output is indicated as output 28. In FIGS. 1 and 2 this is clockwise and the output is indicated as output 28. All the blood components move toward the left in FIG. 3 toward closer rotor segment 26a because their densities are smaller and they essentially float on top of the rTAP. In FIGS. 1 and 2 this is counterclockwise and the blood components output is indicated as output 29.

More particularly, as the blood and rTAP continue to be injected into rotor 26a, 26b at input 31 (shown in FIGS. 1-3), the blood components move towards the lower centrifugal field while the rTAP move to the higher centrifugal field. The thickness of belt shaped rotor 24 is only 5 mm according to one embodiment. The separation of the rTAP and blood is carried out very quickly and form layers based are density of the particles. With separation being accomplished quickly it is possible maintain the rate of rTAP and blood inflow sufficiently fast to make the process "continuous-flow density separation". As mentioned above the rTAP leave the rotor at output 28 at the end of highest centrifugal force, while the blood components move leave the rotor at output 29 at the end of lowest centrifugal force. The semicircular rotor has a small offset, bend and protrusion near the junction of segments 26a and 26b to make the separation of rTAP from the blood complete. In FIGS. 1, 2 and 3 this is indicated by the number 40, but offset 40 is best seen in FIGS. 2 and 3. More specifically, it is possible to enhance the change of centrifugal force by creating a protrusion at the site where distinctive separation of two layers is made, since their sedimentation coefficients are predominantly a function of $(1-\rho/\delta)$, the particulates will be positioned close to the outer wall of the rotor when the density equilibrium is established.

Near at the exit port 28 of the rTAP, there is a monitor output port 30, from which small samples are taken of the particles flowing toward its output 28 to test the purity of the rTAP. The purity of the rTAP might change slowly over time during centrifugal retrieval of the rTAP so the relative flow rates of pumps must be adjusted to maintain the purity of the rTAP output at its port 28. Under a given revolution per minute of the rotor, to achieve the optimal removal of rTAP from the blood, using the notation in FIG. 1, the following flow conditions must be met according to one embodiment of the present invention. F31=F28+F29+F30 wherein F stands for flow rate. Each flow rate may be controlled by the corresponding monitor/pump, except the flow rate at tube 30 (RBC). The liquid flow rate of the blood entering into the rotor through tube 31, will be set by the pump P31 at the desired flow rate. The RBC monitors will be mounted at both tubes 28 and 29, so that there would be little RBC going through either tube by adjusting the flow rate controlled by the pump for each tube. In short, all blood components will be collected through only tube 30, and the plasma through tube 29 and the highest density particles through tube 28.

According to one embodiment of the system and method of the present invention a rotor separates the components in the blood or fluid or solution according to their densities. Some of the components may be attached to high density sub-micron particles and thus they can be separated exclusively from all the blood components or the fluid or the solution. The process of separation can be done during continuous flow of the liquid through the device. The density separation is made possible with the rotor made of connecting at least two rectangular or other forms having a void within for receiving fluid or solution or blood and the forms are curved or circularly bent with two slightly different diameters of them each no longer than ¼ of the circle. The forms are mounted on the circular disc. The circular disc having a hole in the center to form a base of the rotor. A number of tubes connect to openings in the rotor such that the rotor connects fluid that flows via a tube to the rotor with one or more tubes that carry fluid that flows out of the rotor. The tubes may follow a path through the center whole and are configured so that the base will be able to continuously spin, along with the mounted rotor elements without interference from the one or more tubes. One of the tubes is connected through a port to the inner wall of the larger segment rotor and the blood or liquid will enter through the port by a pump, of which rate can be adjusted. The particles that enter the rotor will be separated according to their densities and pour out from the ports 28 and 29. The rates of outflows will be regulated with two pumps, one pump for each port. From port 29 the lowest density matter (plasma) and port 28 the highest density matter such as rTAP bound with the target will flow out by the pumps. There is a third exit port 30 from which the particles next to the highest density particles, rTAP, such as RBC will exit. The separation will be done continuously with less than 100 ml of the samples in the rotor and feeding tubes. The entire amount of sample will be treated and collected after rising the rotor and feeding tubes.

The novel density gradient separation technique taught and claimed herein may be used to separate other mixtures of substances having different densities. It may be used to separate and remove metastatic cancer cells from circulating blood. It may also be used for retrieval of low copy mammalian, bacterial or virus cells from blood. It may also be used to remove materials added to blood to enhance tissue and organ imaging. Depending on the application, the specific design requirement of these materials in terms of their size and composition may vary, but common to all of them are the properties summarized earlier, and the tailored ability for continuous retrieval from circulating fluids.

While what has been described herein is the preferred embodiment of the invention it will be understood by those skilled in the art that numerous changes may be made without departing from the spirit and scope of the invention.

What is claimed is:

1. A rotor for a centrifuge used to separate a mixture of components in a fluid having different densities, the rotor comprising:
    a circular rotor base having a central axis wherein the rotor base is rotated about the central axis when the centrifuge is in use;
    a first rotor element that is curved and has an orientation extending away from the rotor base, the first rotor element having a first end and a second end;
    a second rotor element that is curved and has an orientation extending away from the rotor base, the second rotor element having a first end and a second end, the second end of the first rotor element being continuous with the first end of the second rotor element via a step-down offset in the curve of the first rotor element to form a composite rotor element; wherein the composite rotor element is positioned on the rotor base so that the distance (d4) of the first end of the first rotor element and the distance (d3) of the second end of the second rotor element are at different distances from the central axis wherein the distance d4>d3;
    the composite rotor element forming an arc of only 180° relative to the axis of rotation of the rotor base; and
    an input port, a first output port and monitor output port are positioned on the first rotor element.

2. The centrifuge rotor of claim 1 wherein when operational and rotating with a fluid mixture of components therein a density gradient is created in the first and the second rotor elements of the composite rotor due to their orientation on the rotor base and provides that the components of the mixture within the rotor elements are separated into two different density groups, a first of the two components moves in a first direction inside the first rotor element and is removed from the first output port while a second of the two components having a density that is different from the first of the two components moves in a second, opposite direction and is removed from a second output port.

3. The centrifuge rotor of claim 2 wherein:
    the monitor output port being positioned closer to the first output port at the first end of the first rotor element than as compared to the input port, and is used to extract a sample of the fluid mixture of components, the sample being used to determine if the first of the two components has been separated from the second of the two components.

4. The centrifuge rotor of claim 2 further comprising:
    a sensor connected to the monitor output port to monitor the second of the two components; and
    electronics receiving an output signal from the sensor, the electronics causing a change in a rate at which the first of the two components is removed from the centrifuge at the first output port, and changing a rate at which the second of the two components is removed from the centrifuge at the second output port to eliminate the presence of the second of the two components in a sample of the fluid mixture of components taken at the monitor output port, thus assuring there is none of the second of the two components present with the first of the two components exiting the centrifuge at the monitor output port.

5. The centrifuge rotor of claim 4 wherein the electronics also causes a change in a rate at which the mixture of components is input to the composite rotor element to assure there is none of the first of the two components present with the second of the two components exiting the composite rotor element at the monitor output port.

6. A method of separating components in a fluid based upon a difference in density of the components in the fluid when the components are mixed together comprising the steps:
    providing to the rotor of claim 1 the fluid containing the mixed together components to be separated based upon the difference in density of the mixed together components;
    continuously flowing the components in the fluid to the rotor while the rotor is spinning;
    separating the components in the fluid based upon the difference in density of the mixed together components with the use of centrifugal force when the rotor is spinning;
    collecting components having: i) a first density via the first output port located at a first end of the first rotor element, ii) a second density via the monitor port located at a second position on the first rotor element, and iii) a third density via a second output port on the second rotor element.

7. The method of claim 6 wherein the components having the first density comprise high density sub-micron particles that have a greater density than the components with the second density or the third density.

8. The method of claim 7 wherein the high density sub-micron particles are functionalized to capture a first target in the fluid to be passed through the rotor element.

9. The method of claim 7 wherein the components having the first density have the greatest density.

10. The method of claim 9 wherein the components having the first density are collected at the first output port of the first rotor element.

11. The method of claim 10 wherein the components having the second density are heavier than the components having the third density.

12. The method of claim 11 wherein the monitor output port is positioned between the first output and the input port on the first rotor element.

13. The method of claim 12 wherein the second output port is positioned on the second end of the second rotor element.

14. The method of claim 13 wherein the components having the third density are collected at the second output port.

15. A rotor for a centrifuge used to separate a mixture of components in a fluid having different densities, the rotor comprising:
    a first rotor element that is curved and having a first end and a second end;
    a second rotor element that is curved having a first end and a second end, the second end of the first rotor element being continuous with the first end of the second rotor element via a step-down offset in the curve of the first rotor element to form a composite rotor element;
    wherein the composite rotor element is intended for use on a rotor base, the composite rotor element forms an arc of only 180° relative to the axis of rotation of the rotor base so that the distance (d4) of the first end of the first rotor element and the distance (d3) of the second end of the second rotor element are at different distances from the central axis wherein the distance d4>d3; and
    an input port, a first output port and a monitor output port are positioned on the first rotor element.

16. The rotor of claim 15, when positioned on the rotor base for use, has an orientation extending away from the rotor base.

17. The rotor of claim 15 has a cavity within the composite rotor to accept a the mixture of components in the fluid such that a density gradient forms in the composite rotor and separates the fluid into two distinct density groups, a first density group of components which moves in a first direction inside the first rotor element and is removed from the first rotor element at the first output port and a second density group of components that moves to a second position inside the composite rotor and is removed from the first rotor element at the monitor output port when the rotor is positioned on the rotor base that is rotating.

18. The rotor of claim 15 wherein:
the monitor output port of the first rotor element is positioned closer to the first output port at the first end of the first rotor element than as compared to the input port position.

19. The rotor of claim 17 further comprising:
a sensor connected to the monitor output port to monitor the second density group of components for the presence of the first density group of components, the sensor generating an output signal if any of the first density group of components is present; and
electronics receiving the output signal from the sensor and causing a change to a flow rate at i) the first output port, ii) the monitor output port or iii) the input port in response to the signal from the sensor.

20. The rotor of claim 19 wherein the electronics cause a change in a rate at which the first density group of components is removed from the rotor at the first output port.

21. The rotor of claim 19 wherein the electronics cause a change in a rate at which the second density group of components is removed from the rotor at the monitor output port wherein the change in the rate decreases the presence of the first density group of components in the sample taken at the monitor output port.

22. The rotor of claim 19 wherein the electronics cause a change in a rate at which the fluid enters the composite rotor element through the input port to decrease the presence of the first density group of components present in the sample of the second density group of components exiting the composite rotor element at the monitor output port.

* * * * *